United States Patent [19]

Kampmann et al.

[11] Patent Number: 5,055,618
[45] Date of Patent: Oct. 8, 1991

[54] PROCESS FOR THE PREPARATION OF α,ω-DIAMINES

[75] Inventors: Detlef Kampmann, Bochum; Jürgen Weber; Claus Kniep, both of Oberhausen, all of Fed. Rep. of Germany

[73] Assignee: Hoechst Aktiengesellschaft, Fed. Rep. of Germany

[21] Appl. No.: 527,112

[22] Filed: May 21, 1990

[30] Foreign Application Priority Data

May 30, 1989 [DE] Fed. Rep. of Germany ....... 3917444

[51] Int. Cl.⁵ .......................................... C07C 209/26
[52] U.S. Cl. .................................. 564/473; 564/445; 564/446; 564/470
[58] Field of Search ................ 564/473, 470, 445, 446

[56] References Cited

U.S. PATENT DOCUMENTS

| 3,346,640 | 10/1967 | Guyer et al. | 260/583 |
| 3,565,954 | 12/1971 | Bouniot | 564/473 |
| 3,707,563 | 12/1972 | Pikl | 564/473 |
| 4,855,505 | 8/1989 | Köll | 564/398 |
| 4,952,734 | 8/1990 | Weber et al. | 564/471 |

FOREIGN PATENT DOCUMENTS 0663294 12/1951 United Kingdom .
1520969 8/1978 United Kingdom .

Primary Examiner—Glennon H. Hollrah
Assistant Examiner—Peter G. O'Sullivan
Attorney, Agent, or Firm—Jordan B. Bierman; Bierman and Muserlian

[57] ABSTRACT

The object of this invention is the preparation of α,ω-diamines from α, ω-dialdehydes in a method which comprises the reaction of a starting mixture of said dialdehyde, a primary amine, and water to form a reaction mixture, followed by treatment of said reaction mixture with excess ammonia and hydrogen in the presence of a hydrogenation catalyst to produce a final mixture.

76 Claims, No Drawings

PROCESS FOR THE PREPARATION OF α,ω-DIAMINES

The present invention relates to a process for the preparation of a α,ω-diamines from α,ω-dialdehydes.

BACKGROUND OF THE INVENTION

Such diamines have great importance due to the chemical properties resulting from their two terminal amino groups. They are required, inter alia, for the preparation of plastics, e.g. polyamides and specific alkyd resins, and for the production of fabric finishes and adhesives. Condensation of diamines with dicarboxylic acids is used to obtain wetting agents and emulsifiers which are especially useful in the oil industry. Diamines are, moreover, particularly suitable as hardeners in epoxy resins.

These α,ω-diamines can be prepared by various methods; for example, by reduction of dinitriles. However, it has to be borne in mind that the dinitriles required as starting materials are not readily available, but rather can be obtained only by a synthesis involving many steps. For this reason, this method is not commercially important.

If cyclic olefins, for example cyclohexene, are treated with ozone, the corresponding ozonides are obtained, which can be converted into the corresponding diamines by reductive amination. U.S. Pat. No. 2,657,240 describes a process of this type. The yield of diamine which is achievable is only about 30% relative to the cyclohexene used. Transfer of this process to the industrial scale is limited, not only due to the complex preparation and difficult handling of ozone, but also due to the low yield.

German Offenlegungsschrift 2,824,423 describes a two-step process for the preparation of diamines by the reaction of dialdehydes with a monoamine and subsequent treatment of the reaction product with ammonia and hydrogen in the presence of a hydrogenation catalyst. In order to achieve yields which allow the commercial use of the process, it is, however, necessary to use the monoamine in large excess in relation to the dialdehyde.

German Offenlegungsschrift 2,647,317 relates to a two-step process for the preparation of α,ω-diamines by reductive amination of the corresponding dialdehydes. In a first step, the dialdehyde is reacted with ammonia at a low temperature in the presence of a mixture comprising water and an organic solvent, a diimine being formed from the dialdehyde with the elimination of water. This diimine is reacted in a second step by catalytic reduction to form the α,ω-diamine. The α,ω-diamine yield achievable is dependent to a large extent on the temperature used in the preparation of the diimine. The lower this temperature, the higher the yield. Temperatures in the range of $-5°$ to $-10°$ C. produce yields of between about 80 to 90% based on the dialdehyde. If the temperature of diimine formation is increased even slightly (for example to $+5°$ C.), the α,ω-diamine yield is greatly reduced and the formation of undesired by-products increases sharply. The low temperature which is necessary for diimine formation precludes the use of this process; industrially, low temperatures of this type can only be achieved at great cost.

BRIEF DESCRIPTION OF THE INVENTION

The object is therefore to provide a process which avoids the previously described disadvantages, can be readily applied, and allows the reaction to be carried out even at relatively high temperatures.

This object is achieved by reacting an α,ω-dialdehyde with a primary amine in the presence of water and treating the reaction mixture in the presence of a hydrogenation catalyst with excess ammonia and hydrogen, whereby the corresponding α,ω-diamine is formed.

An essential feature of the novel process is the presence of water in the reaction of the dialdehyde and the primary amine. Surprisingly, as a result of this measure, both the conversion and the selectivity of the reaction can be improved. If, due to the preparation, the α,ω-dialdehyde is present as a mixture of n- and iso-dialdehydes, the addition of water furthermore favors the formation of the desired diamine resulting from the n-dialdehyde, while the conversion of the iso-dialdehyde to the corresponding diamine is suppressed.

DETAILED DESCRIPTION OF THE INVENTION

The reaction of the α,ω-dialdehyde with the primary amine in the presence of water can be carried out at $0°$ to $60°$ C. In many cases, the reaction will be carried out at $10°$ to $55°$ C. It has proved particularly favorable to react the α,ω-dialdehyde with the primary amine in the presence of water at 20 to 50, preferably $30°$ to $50°$ C.

According to the novel process, any desired α,ω-dialdehydes can be reacted, particularly aliphatic straightchain, branched or cyclic α,ω-dialdehydes. These preferably include straightchain and cyclic α,ω-dialdehydes having 2 to 16, preferably 4 to 14, preferably 6 to 12 carbon atoms. Examples of useful α,ω-dialdehydes are 1,4-butanedial, 1,6-hexanedial, 1,8-octanedial, 1,10-decanedial, 1,12-dodecanedial, bisformyltricyclo[5.2.1.0$^{2,6}$]-decane; particularly 1,6-hexanedial, 1,8-octanedial, 1,10-decane-dial, 1,12-dodecanedial, preferably 1,8-octanedial, 1,10-decanedial and 1,12-dodecanedial. The α,ω-dialdehydes required for the reaction can be prepared using conventional processes described in the literature.

Where the primary amines are concerned, no restrictions are imposed. However, highly suitable primary aliphatic amines are those which are straightchain, branched or cyclic, particularly branched or straightchain. Primary aliphatic amines having 2 to 6, particularly 3 to 5 carbon atoms have proved particularly suitable. Examples of useful primary amines are ethylamine, n-propylamine, isopropylamine, n-butylamine, isobutylamine, n-pentylamine, 2-methylbutylamine, 3-methylbutylamine, and n-hexylamine; particularly ethylamine, n-propylamine, n-butylamine, and n-pentylamine; preferable are ethylamine, n-propylamine and n-butylamine.

It has proved desirable to react the α,ω-dialdehyde with the primary amine dissolved in water. The concentration of the primary amine in the water is normally 10 to 90, particularly 20 to 80, preferably 30 to 70% by weight. In a further advantageous embodiment of the process according to the invention, α,ω-dialdehyde is used as a mixture with water. These mixtures generally contain 30 to 70% by weight, particularly 35 to 65% by weight of α,ω-dialdehyde and 70 to 30, particularly 65 to 35% by weight of water.

The α,ω-dialdehyde can be admixed with the primary amine dissolved in water, or a mixture comprising the dialdehyde and water can be admixed with the primary amine dissolved in water. It is important for the success of the reaction that the α,ω-dialdehyde is always reacted with an amount of primary amine which is adequate for formation of the desired azomethine (Schiff's base). In this reaction the primary amine should be present as far as possible in excess in relation to the reacting aldehyde groups. Usually the total amount or a partial amount of the primary amine is initially charged and the α,ω-dialdehyde is metered in. Thorough mixing of the normally heterogeneous mixture is to be ensured, for example by intensive stirring.

The process may be carried out batchwise or continuously. If the process is operated batchwise, the primary amine is initially charged and the α,ω-dialdehyde is added in a continuous stream or in portions with stirring.

If the process is operated continuously, it has to be ensured that the reacting α,ω-dialdehyde is always supplied with sufficient primary amine as co-reactant. The rapid, complete formation of the Schiff base is important for the success of the process according to the invention. Otherwise, the α,ω-dialdehyde reacts to form undesired by-products; for example, aldolization reactions and condensation and polymerization reactions which are catalyzed by the primary amine.

The α,ω-dialdehyde and the primary amine are reacted in the molar ratio of 1:2 to 1:3, particularly 1:2.05 to 1:2.4, preferably 1:2.1 to 1:2.25. It often proves advantageous to use the primary amine in excess of these amounts. A stoichiometric excess of the primary amine of 5, particularly 8, preferably 10% is adequate in most cases.

The reaction of the α,ω-dialdehyde with the primary amine forms the corresponding α,ω-diazomethine with the elimination of water. The resulting reaction mixture generally comprises two phases, namely, an organic phase and an aqueous phase. The organic phase contains the α,ω-diazomethine, minor quantities of dissolved water and possibly portions of the primary amine used in excess.

In addition to small amounts of dissolved α,ω-diazomethine and possibly of the primary amine used in excess, the aqueous phase is composed for the most part of water which enters the reaction mixture with the starting materials on the one hand and, on the other hand, is due to the liberation of water from the reaction.

The foregoing reaction mixture is reacted with excess ammonia and hydrogen in a subsequent step in the presence of a hydrogenation catalyst in the liquid phase in the manner of an aminating hydrogenation to form the desired α,ω-diamine. 5 to 50, particularly 10 to 40, preferably 15 to 30 moles of $NH_3$ and at least the stoichiometrically required amount of $H_2$ are used per mole of α,ω-dialdehyde initially used. Excess ammonia and hydrogen can be recycled into the reaction. The reaction is favored by increasing the temperature and the pressure. The reaction temperature should be 30° to 180°, particularly 50° to 150°, preferably 80° to 130° C. and the reaction pressure should be 0.5 to 30, particularly 1 to 15, preferably 5 to 12 MPa. If the reaction is to be carried out under mild conditions, lower temperatures are used, for example <100°, particularly <90°, preferably <80° C. If a faster reaction is desired, higher reaction temperatures are used, for example >100°, particularly >110°, preferably >120° C. The desired pressure is adjusted by the addition of $H_2$.

With regard to the course of the reaction, it may be assumed that the corresponding α,ω-diimine is formed as an intermediate from the α,ω-diazomethine by the action of $NH_3$. The desired α,ω-diamine is formed from this intermediate diimine by reduction with $H_2$. The reaction may be carried out batchwise or continuously.

Hydrogenation catalysts used may be available catalysts containing for example Cu, Co and/or Ni as the active hydrogenating component. Water-resistant Ni-containing catalysts are particularly suitable. These catalysts have 40 to 70% by weight, particularly 45 to 65% by weight, preferably 55 to 62% by weight of nickel relative to the total catalyst composition. Carriers used are pumice stone, aluminum oxide, siliceous earth and alumina and $SiO_2$ in its various forms. Activators used are compounds containing alkaline earth metals, aluminum, zinc and/or chromium. It is also possible to use a nickel catalyst without a carrier, for example Raney-nickel, as a catalyst.

The space velocity (liquid volume of product per dry volume of catalyst per hour) depends on the reaction conditions selected. It is 0.1 to 1.0, particularly 0.15 to 0.5, preferably 0.2 to 0.35, per hour.

The catalyst may be arranged fixed, for example in the form of a bed over which the mixture of starting materials is fed, or may be present suspended as a slurry. If it is intended to carry out the reaction with a fixed-bed catalyst, it can be advantageous to convert the mixture of starting materials into a homogeneous form by adding a suitable solvent, and then feeding this to the catalyst. It can occassionally be advantageous, before carrying out the reduction amination, to separate out a portion of the aqueous phase from the mixture of starting materials or to convert the mixture of starting materials into a homogenous form by the addition of a suitable solvent.

According to a preferred embodiment, the hydrogenation catalyst is placed in suspension and the mixture of starting materials is added to the catalyst slurry. The suspending agent used can be the primary amine, crude reaction product, or else previously formed α,ω-diamine.

The course of the reaction being that of a reductive amination, the hydrogenation of the reaction mixture containing the α,ω-diazomethine should always be carried out in the presence of an excess of $NH_3$. In this way, it is ensured that the α,ω-diazomethine splits off the primary amine originally used, the α,ω-diimine forms as an intermediate, and the latter is converted into the corresponding α,ω-diamine.

At the end of the reaction, a homogeneous product is present which is composed of the desired α,ω-diamine, water, the primary amine, excess ammonia and possibly minor amounts of hydrogen and by-products. The gaseous components of the reaction mixture are separated off and the α,ω-diamine is purified by distillation.

The following examples illustrate the present invention without limiting it:

EXPERIMENTAL PART

EXAMPLE 1

263 g (3.6 mol) of n-butylamine and 260 g of water are initially introduced into a 2 liter three-necked flask equipped with a stirrer, dropping funnel, dip pipe, thermometer, and reflux condenser. An emulsion, composed of 213 g (1.5 mol) of octanedial (n/iso ratio 80:20) and 200 g of water, is added to the n-butylamine-water mixture via the dip pipe with stirring over a period of 60 minutes. The emulsion in the dropping funnel is kept constantly agitated by bubbling in a stream of nitrogen so that the mixture does not separate.

The temperature is 40° C. during the addition of the emulsion. At the end of the addition, the reaction of the mixture is allowed to continue for an additional 2 hours with stirring at 40° C.

The reaction mixture obtained comprises two phases, an upper organic layer and a lower aqueous layer. The mixture is transferred to an autoclave equipped with a stirrer and to it are added 47 g of a nickel catalyst containing a carrier (50 to 54% by weight of Ni, a commercial product from Hoechst AG: RCH Ni 52/35) and a 20-fold molar excess of $NH_3$. A pressure of 10 MPa is established by compressing the hydrogen. Hydrogenation is carried out with stirring at 120° C. for a period of 4 hours resulting in a homogeneous hydrogenation mixture. It has the composition given below (ignoring added water, formed water, and ammonia), determined by gas chromatographic analysis:

| forerun | 0.1% by weight |
|---|---|
| n-butylamine | 51.5% by weight |
| 2,5-dimethyl-1,6-diaminohexane | 0.1% by weight |
| 2-methyl-1,7-diaminoheptane | 9.4% by weight |
| 1,8-diaminooctane | 38.2% by weight |
| after-run | 0.7% by weight |

After distillation in a column with 9 theoretical plates, the diamine is obtained in a yield of 81.7% (selectivity 95%).

COMPARISON EXAMPLE 1

The procedure followed in Example 1 is repeated but without the addition of water.

According to gas chromatographic analysis, the resulting hydrogenated mixture has the following composition (ignoring water formed and ammonia).

| forerun | 2.5% by weight |
|---|---|
| n-butylamine | 45.4% by weight |
| 2,5-dimethyl-1,6-diaminohexane | 3.0% by weight |
| 2-methyl-1,7-diaminoheptane | 4.7% by weight |
| 1,8-diaminooctane | 26.1% by weight |
| after-run | 18.3% by weight |

After distillation in a column having 9 theoretical plates, the diamine is obtained in a yield of only 60.2%.

EXAMPLE 2

567 g (7.76 mol) of n-butylamine and 567 g of $H_2O$ are initially introduced into a 4 liter three-necked flask equipped with a stirrer, dropping funnel, dip pipe, thermometer, and reflux condenser. An emulsion, composed of 750 g (7.05 mol) of bisformyltricyclo$[5.2.1.0^{2,6}]$-decane (crude product) and 750 g of water, is added to the n-butylamine-water mixture via the dip pipe with stirring over a period of 90 minutes. The emulsion in the dropping funnel is kept constantly agitated by bubbling in a stream of nitrogen so that the mixture does not separate. The temperature is 40° to 42° C. while the emulsion is being added. At the end of the addition, the mixture is allowed to react for an additional 2 hours with stirring at 40° C.

The reaction mixture obtained comprises two phases, an upper organic layer and a lower aqueous layer. It is transferred to an autoclave equipped with a stirrer and hydrogenated as described in Example 1. The resulting homogeneous hydrogenated mixture has the following composition (ignoring added water, formed water, and ammonia), determined by gas chromatographic analysis:

| n-butylamine | 43.6% by weight |
|---|---|
| forerun + isomeric monoamines | 0.2% by weight |
| TCD*-monmoamine | 5.5% by weight |
| forerun + isomeric diamines | 1.6% by weight |
| TCD*-diamine | 43.4% by weight |
| TCD*-hydroxyamine | 1.2% by weight |
| TCD*-diol + higher boiling components | 4.5% by weight |

*TCD = tricyclo$[5.2.1.0^{2,6}]$-decane

The bis-(aminomethyl)-tricyclo$[5.2.1.0^{2,6}]$-decane yield (TCD-diamine yield) is about 95%, relative to the dialdehyde used.

COMPARISON EXAMPLE 2

The procedure followed in Example 2 is repeated but without the addition of water.

As determined by gas chromatographic analysis, the resulting hydrogenated mixture has the following composition (ignoring formed water, and ammonia):

| n-butylamine | 40.3% by weight |
|---|---|
| forerun + isomeric monoamines | 0.2% by weight |
| TCD*monoamine | 4.9% by weight |
| forerun + isomeric diamines | 1.4% by weight |
| TCD*-diamine | 38.4% by weight |
| TCD*-hydroxyamine | 1.1% by weight |
| TCD*-diol + higher boiling components | 13.7% by weight |

*TCD = tricyclo$[5.2.1.0^{2,6}]$-decane

The bis-(aminomethyl)-tricyclo$[5.2.1.0^{2,6}]$-decane yield TDC-diamine yield) is only about 84%, relative to the dialdehyde used.

What is claim is:

1. A method for the preparation of $\alpha,\omega$-diamines from $\alpha,\omega$-dialdehydes comprising reaction of a starting mixture comprising said dialdehyde, a primary amine, and water to form a reaction mixture, followed by treatment of said reaction mixture with excess ammonia and hydrogen in the presence of a hydrogenation catalyst to produce a final mixture.

2. The method of claim 1 wherein said starting mixture contains sufficient said primary amine to form a Schiff base with said dialdehyde.

3. The method of claim 1 wherein said reaction takes place at a reaction temperature of 0° to 60° C.

4. The method of claim 3 wherein said reaction temperature is 10° to 55° C.

5. The method of claim 4 wherein said reaction temperature is 20° to 50° C.

6. The method of claim 5 wherein said reaction temperature is 30° to 50° C.

7. The method of claim 1 wherein said dialdehyde is straight chain or cyclic.

8. The method of claim 1 wherein said dialdehyde has 2 to 16 carbon atoms.

9. The method of claim 8 wherein said dialdehyde has 4 to 14 carbon atoms.

10. The method of claim 9 wherein said dialdehyde has 6 to 12 carbon atoms.

11. The method of claim 1 wherein said dialdehydes are selected from the group consisting of 1,4-butanedial, 1,6-hexenedial, 1,8-octanedial, 1,10-decanedial, 1,12-dodecanedial, and bisformyltricyclo[5.2.1.0$^{2,6}$]-decane.

12. The method of claim 11 wherein said dialdehyde is selected from the group consisting of 1,6-hexanedial, 1,8-octanedial, 1,10-decanedial, and 1,12-dodecanedial.

13. The method of claim 12 wherein said dialdehyde is selected from the group consisting of 1,8-octanedial, 1,10-decanedial, and 1,12-dodecanedial.

14. The method of claim 1 wherein said primary amine is aliphatic branched or straight chain.

15. The method of claim 4 wherein said primary amine has 2 to 6 carbon atoms.

16. The method of claim 15 wherein said primary amine has 3 to 5 carbon atoms.

17. The method of claim 1 wherein said primary amine is selected from the group consisting of ethylamine, n-propylamine, isopropylamine, n-butylamine, isobutylamine, n-pentylamine, 2-methylbutylamine, 3-methylbutylamine, and n-hexylamine.

18. The method of claim 17 wherein said primary amine is selected from the group consisting of ethylamine, n-propylamine, n-butylamine, and n-pentylamine.

19. The method of claim 18 wherein said primary amine is selected from the group consisting of ethylamine, n-propylamine, and n-butylamine.

20. The method of claim 1 wherein said dialdehyde is mixed with a water solution of said primary amine to form said starting mixture.

21. The method of claim 20 wherein said water solution contains 10% to 90% by weight of said primary amine.

22. The method of claim 21 wherein said water solution contains 20% to 80% by weight of said primary amine.

23. The method of claim 22 wherein said water solution contains 30% to 70% by weight of said primary amine.

24. The method of claim 20 wherein said dialdehyde is in aqueous solution.

25. The method of claim 21 wherein said aqueous solution contains 30% to 70% of said dialdehyde, the remainder being water.

26. The method of claim 22 wherein said aqueous solution contains 35% to 65% of said dialdehyde, the remainder being water.

27. The method of claim 23 wherein said primary amine is present in stoichiometric excess of said dialdehyde in said reaction.

28. The method of claim 1 wherein said dialdehyde is added to said primary amine to form said starting solution.

29. The method of claim 28 wherein said dialdehyde is added continuously.

30. The method of claim 28 wherein said dialdehyde is added portionwise.

31. The method of claim 1 wherein said starting mixture is stirred.

32. The method of claim 1 wherein said reaction is continuous.

33. The method of claim 32 wherein said reaction is carried out batchwise.

34. The method of claim 1 wherein the mol ratio of said aldehyde to said amine in said reaction is 1.2 to 1.3.

35. The method of claim 34 wherein said mol ratio is 1:20.05 to 1:2.4.

36. The method of claim 35 wherein said mol ratio is 1:2.1 to 1:2.25.

37. The method of claim 1 wherein 5 to 50 mols of said ammonia per mol of said aldehyde are added to said reaction mixture.

38. The method of claim 37 wherein 10 to 40 mols of said ammonia per mol of said aldehyde are added to said reaction mixture.

39. The method of claim 38 wherein 15 to 30 mols of said ammonia per mol of said aldehyde are added to said reaction mixture.

40. The method of claim 1 wherein a stoichiometric amount of said hydrogen is present in said reaction mixture.

41. The method of claim 1 wherein said treatment is carried out at elevated temperature.

42. The method of claim 41 wherein said treatment is carried out at a treatment temperature of 30° to 180° C.

43. The method of claim 42 wherein said treatment temperature is 50° to 150° C.

44. The method of claim 43 wherein said treatment temperature is 80° to 130° C.

45. The method of claim 1 wherein said treatment is carried out at an elevated treatment pressure.

46. The method of claim 45 wherein said treatment preasure is 0.5 to 30 MPa.

47. The method of claim 46 wherein said treatment pressure is 1 to 15 MPa.

48. The method of claim 47 wherein said treatment pressure is 5 to 12 MPa.

49. The method of claim 1 wherein said treatment is carried out at less than 100° C.

50. The method of claim 49 wherein said treatment is carried out at less than 90° C.

51. The method of claim 50 wherein said treatment is carried out at less than 80° C.

52. The method of claim 1 wherein said treatment is carried out at more than 100° C.

53. The method of claim 52 wherein said treatment is carried out at more than 110° C.

54. The method of claim 53 wherein said treatment is carried out at more than 120° C.

55. The process of claim 45 wherein said treatment pressure is adjusted by addition of hydrogen.

56. The process of claim 1 wherein said treatment is continuous.

57. The process of claim 1 wherein said treatment is batchwise.

58. The process of claim 1 wherein said catalyst comprises copper, cobalt, and/or nickel.

59. The process of claim 58 wherein said catalyst contains nickel as a catalytically active metal.

60. The process of claim 59 wherein said nickel is water resistant.

61. The process of claim 59 wherein said catalyst contains 40% to 70% by weight of said nickel.

62. The process of claim 61 wherein said catalyst contains 45% to 65% by weight of said nickel.

63. The process of claim 62 wherein said catalyst contains 55% to 62% by weight of said nickel.

64. The process of claim 1 wherein said catalyst is Raney nickel and no carrier is present.

65. The method of claim 1 wherein said catalyst is on a carrier.

66. The method of claim 65 wherein said carrier is selected from the group consisting of pumice, aluminum oxides, siliceous earth, and $SiO_2$.

67. The method of claim 1 wherein said catalyst contains an actuator.

68. The method of claim 67 wherein said actuator is selected from the group consisting of alkaline earth metals, aluminum, zinc, and/or chronium.

69. The method of claim 1 wherein said treatment is carried out at a space velocity of 0.1 to 1.0 per hour.

70. The method of claim 69 wherein said space velocity is 0.15 to 0.5 per hour.

71. The method of claim 70 wherein said space velocity is 0.2 to 0.35 per hour.

72. The method of claim 1 wherein said catalyst is a fixed bed.

73. The method of claim 72 wherein said starting mixture comprises a solvent, said starting mixture being fed to said catalyst.

74. The method of claim 1 wherein said catalyst is in suspension and said starting mixture is added thereto.

75. The method of claim 74 wherein said catalyst is suspended by a suspending agent selected from the group consisting of said primary amine, said reaction mixture, said diamine, and mixtures thereof.

76. The method of claim 1 wherein said reaction mixture is treated with 10 to 40 mols of ammonia and at least a stoichiometric amount of hydrogen, both based on said dialdehyde, at 50° to 150° C. and 1 to 15 MPa, said catalyst being a water resistant nickel catalyst.

* * * * *